United States Patent [19]

Mattes et al.

[11] Patent Number: 4,863,854
[45] Date of Patent: * Sep. 5, 1989

[54] MONOCLONAL ANTIBODIES TO MUCIN-LIKE HUMAN DIFFERENTIATION ANTIGENS

[75] Inventors: M. Jules Mattes, Flushing; John L. Lewis, Jr., New York; Lloyd J. Old, New York; Kenneth O. Floyd, Bronx; Katherine Look, New York, all of N.Y.

[73] Assignee: Sloan-Kettering Institute for Cancer Research, New York, N.Y.

[*] Notice: The portion of the term of this patent subsequent to May 19, 2004 has been disclaimed.

[21] Appl. No.: 764,862

[22] Filed: Aug. 12, 1985

[51] Int. Cl.[4] .................. G01N 33/53; G01N 33/577; C12N 5/00; C07K 15/14
[52] U.S. Cl. .......................................... 435/7; 435/1; 435/172.2; 435/240.27; 436/503; 436/548; 436/813; 530/353; 530/387; 530/828; 530/844; 935/103; 935/105; 935/110
[58] Field of Search ............. 435/68 A, 240.27, 176.2, 435/1, 28; 436/548, 811, 813, 503, 544; 530/387, 353, 828, 843, 844; 935/103, 105, 110

[56] References Cited

U.S. PATENT DOCUMENTS

| | | | |
|---|---|---|---|
| 4,466,917 | 8/1984 | Nussenzweig et al. | 424/88 |
| 4,571,382 | 2/1986 | Adachi | 436/813 |
| 4,626,507 | 12/1986 | Trowbridge et al. | 435/68 |
| 4,666,845 | 5/1987 | Mattes et al. | 436/548 |
| 4,762,800 | 8/1988 | Rettig et al. | 436/548 |

OTHER PUBLICATIONS

Biological Abstract, vol. 79, 1985, Abstract No. 106293, Gangopadhyay et al.
Chemical Abstract, vol. 102, 1985, Abstract No. 111233x, Brockhaus et al.

Primary Examiner—Esther M. Kepplinger
Assistant Examiner—Florina B. Hoffer
Attorney, Agent, or Firm—John P. White

[57] ABSTRACT

Three new monoclonal antibodies, MU78, MT334, and MQ49, and the hybridoma cell lines producing these, are disclosed. The antibodies specifically bind to mucin-like antigens with distribution over various carcinomas.

13 Claims, 4 Drawing Sheets

MONOCLONAL ANTIBODIES TO MUCIN-LIKE HUMAN DIFFERENTIATION ANTIGENS

FIELD OF THE INVENTION

This invention relates to hybridoma cell lines and the monoclonal antibodies produced by these cell lines. More specifically, it relates to monoclonal antibodies which specifically bind to mucin and elastin-type molecules, the antigens determined by the antibodies, and the use of the antibodies in detecting and diagnosing various cancers.

DESCRIPTION OF PRIOR ART

In 1975, Köhler and Milstein published their now well known method for production of mouse/human hybridoma cell lines. By immunizing a murine animal, such as a mouse, with samples of human cancer cells, antibody producing cells are generated by the mouse specimen. These cells are then fused with an immortal human cell line which does not produce antibodies. As each antibody producing cell produces only one kind of antibody, it is then possible, by screening, to determine hybridoma cell lines which produce a particular, desired antibody. The hybridoma cell line, thus identified, can be cloned to produce great amounts of antibody. The antibody produced is all of one type, and can be traced back to a single clone—hence the term "monoclonal antibody".

Many laboratories have generated mouse monoclonal antibodies, using the technique outlined supra, in an effort to identify tumor specific antigens, or useful tumor markers. See, e.g., K. Lloyd, "Human Tumor Antigens: Detection and Characterization with Monoclonal Antibodies", in *Basic and Clinical Tumor Immunology*, (R.B. Herberman, ed, Marten-Nijhoff, Boston MA), pg. 160–214 (1983). A tumor marker is a molecule which is characteristic of a particular tumor type, and enables one to identify that tumor type in a mixed sample of cells and/or tissues.

A high percentage of restrcted human differentiation antigens have been defined recently by mouse monoclonal antibodies as carbohydrate containing molecules. Magnani et al, Science 212: 55 (1981); Pukel et al, J. Exp. Med. 155: 1133 (1982). For example, Magnani, supra defines a sialyated antigen with a monoclonal antibody designated 19.9. The antigen is a serum marker for pancreatic, colon, and gastric carcinoma. Herlyn et al, J. Clin Immunol 2: 135 (1982). OC 125, a serum marker for ovarian cancer, has been defined by Bast et al, New Engl. J. Med. 309: 883 (1983), and appears to be a mucin related molecule, see e.g., Kawabat et al, Int. J. Gynecol. Pathol 2: 275 (1983). Yet another antigen defined by McGee et al, Lancet ii: 7 (1982), and labelled Ca.1, has some properties of a mucin molecule.

The role of mucins as differentiation antigens has only recently been recognized. Bard et al, Br. J. Cancer 41: 209 (1980), describe tissue-related heterogeneity of mucin-like molecules, using rabbit antisera to human gastrointestinal extracts. In addition, Gold et al, J. Biol. Chem. 256: 6354 (1981), have shown colonic mucins include two antigenically distinct molecules, as identified by rabbit antisera. Fisher et al, J. Histochem Cytochem 32: 681 (1984), describe a panel of lectins which appear to distinguish between mucins produced in different regions of the gastrointestinal tract. Also, Bara et al, Cancer Res. 43: 3885 (1983) have shown that there are tumors which consistently produce mucins antigenically different from those produced by normal cells of the same histological type.

The prior art may be seen to teach that at least some differentiation antigens specific to cancer cells are mucin related molecules. While monoclonal antibodies and antigen have been described, no mention or suggestion is made in the prior art of the monoclonal antibodies, the hybridoma cell lines, the antigens, or the methods described and claimed by this invention.

SUMMARY OF THE INVENTION

Monoclonal antibodies MU78, MQ49, and MT334 are described, as well as the hybridoma cell lines which produce them, the antigens defined by the antibodies, and methods of using the monoclonal antibodies.

DETAILED DESCRIPTION OF PREFERRED EMBODIMENTS

Figure 1:
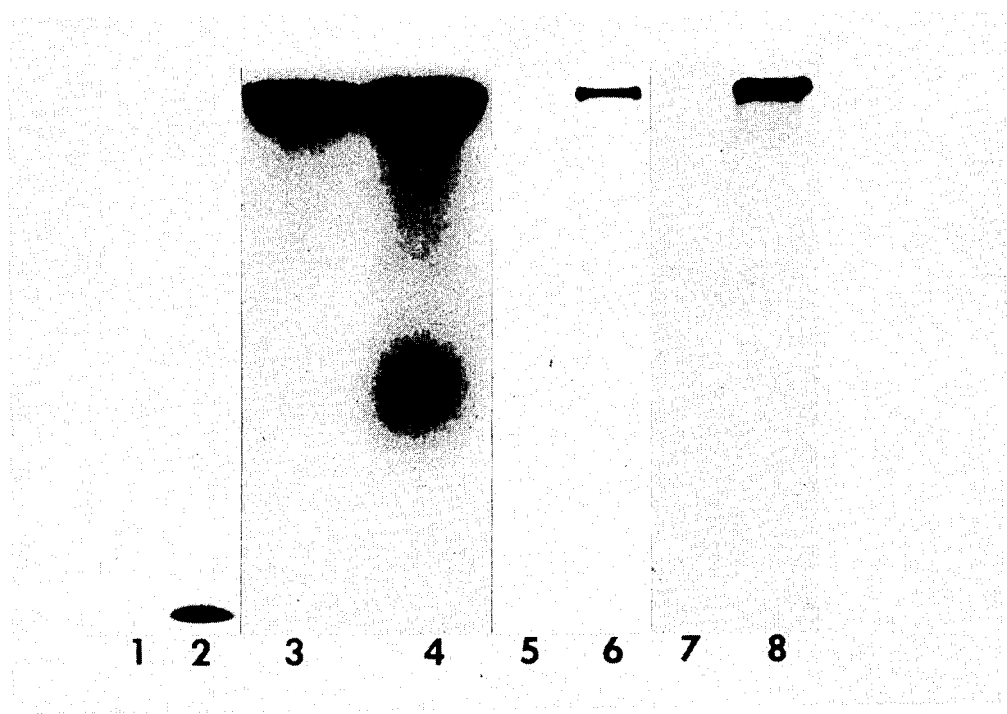
FIG. 1 shows immunoprecipitates of labeled cell extracts as analyzed by PAGE. The antigen used was $^{125}$I-labelled solubilized membrane from cell line SK-OV-4 (lanes 1–4); $^3$H-glucosamine labeled spent medium from cell line SK-UT-2 (lanes 7–8). Gels used were 7.5% acrylamide, (lanes 5–8), 12.5% acrylamide (lanes 1–2), and urea-modified 12.5% acrylamide (lanes 3–4). Precipitating antibodies were normal nu/nu mouse serum or negative monoclonal antibody at appropriate concentrations (odd numbered lanes), or 0.1 $\mu$l MU78 (lanes 2,4); 1.0$\mu$l MT334 (lane 6) or 0.1 $\mu$l MQ49 (lane 8). Exposure times were 1–7 days. MU78 antigen migrates at the dye front in 12.5% acrylamide gel, but is retarded in urea modified gels.

Hybridoma cell lines producing monoclonal antibodies MU78, MT334, and MQ49 have been deposited with the American Type Culture Collection, Rockville, Md., and have been assigned the following accession numbers:

| CELL-LINE | ACCESSION NUMBER |
|---|---|
| MU78 | HB 9752 |
| MT334 | HB 9751 |
| MQ49 | HB 9750 |

The deposits of HB 9750, HB 9751, and HB 9752 were made pursuant to, and in satisfaction of the requirements of the Budapest Treaty on the International Recognition of the Deposit of Mircroorganisms for the Purposes of Patent Procedure (Budapest Treaty).

PRODUCTION OF MOUSE MONOCLONAL ANTIBODIES (BALB/c×C57BL/6)F mice were immunized with the ovarian carcinoma cell lines SW626 or SK-OV-4.

Intraperitoneal injections of approximately 0.1 ml of packed cells were given 2-5 times at intervals of two weeks. Three days after the last injection, the fusion of immune spleen cells with mouse myeloma MOPC-21 NS/1 cells were performed as described by Mattes et al, Hybridoma 2: 253 (1983).

Initially cells were plated in 480 wells. Hybridoma cultures were subcloned at least twice by limiting dilution in 96-well plates on a feeder layer of normal mouse spleen cells. Culture supernatants were monitored for antibody activity on a panel of cultured cells consisting of the immunizing cell line and other types of human tumor cells. Cloned hybridoma cells were injected subcutaneously into nu/nu mice. Sera from mice with progressively growing tumors were collected and used for serological and biochemical characterization. Antibody subclass was determined by double diffusion in agar with anti-Ig heavy-chain-specific reagents.

SEROLOGICAL PROCEDURES

For adherent target cells, 200-500 trypsinized cells were plated in 0.01 ml wells of Terasaki plates and allowed to adhere overnight. Nonadherent target cells were attached to the wells by pretreating the wells for 45 minutes at room temperature with 0.01 ml concanavalin A at 1.0 mg/ml in Dulbecco's PBS. After washing the plates twice and blotting, target cells in DPBS were added and incubated for 45 minutes at room temperature as described by Mattes et al, J. Immunol. Meth. 61: 145 (1983). The immune rosetting assay has been described by Carey et al, PNAS 73: 3278 (1976). To test for neuraminidase sensitivity, target cells were treated for 1 hour at 37° with *Vibrio cholerae* neuraminidase diluted 1:10 in 0.05 M citrate pH 5.5, 0.1M NaCl, 0.01M $CaCl_2$. To detect cytoplasmic antigens, plated target cells were washed twice with PBS, then fixed with 2.0% buffered formaldehyde as described by Farr et al, J. Immunol. Meth. 47: 129 (1981) for 30 minutes. All incubations were at room temperature. After 2 washes with PBS, they were incubated with 0.05% NP40 in PBS for 15 minutes. After 2 washes with PBS, 5% fetal bovine serum (FBS), monoclonal antibody was added, starting with a 1:500 dilution. After a 45 minute incubation, plates were washed twice, and peroxidase-conjugated rabbit anti-mouse Ig was added for 45 minutes. Following 2 washes with PBS, substrate was added (prepared immediately before use by mixing 1.0 ml 0.05 M acetate buffer pH 5.0, 0.05 ml 3-amino-9-ethyl-carbazole at 4.0 mg/ml in N,N-dimethylformamide, and 0.005 ml 3.0% hydrogen peroxide. Graham et al, J. Histochem Cytochem 13: 150 (1965). After 15 minutes, the plates were washed twice with PBS, once with water, and examined.

Immunoperoxidase staining of sections employed 0.005 mm cryostat sections. Air-dried sections were fixed for 10 minutes at room temperature with 2.0% buffered formaldehyde. Sections were obtained from specimens of normal human liver, kidney, lung, pancreas, brain, skin, colon, thyroid, esophagus, stomach, thymus, testes, uterus, ovary, aorta, spleen and lymph node. A triple sandwich method was used routinely, which comprised monoclonal sera at 1/500, biotinylated horse anti-mouse Ig, and complexes of avidin and biotinylated horseradish peroxidase. For particular tissues that had excessive background with this procedure, namely the kidney, liver and pancreas, a double sandwich assay was used which used monoclonal sera at 1/200 and peroxidase-conjugated rabbit anti-mouse Ig at 1/50. In certain experiments (for some photographs), sections were fixed with methanol for 15 minutes at room temperature, instead of formaldehyde. Paraffin sections, examined in some experiments, were obtained by standard procedures after formaldehyde fixation. After deparaffinization they were processed like frozen sections. For Wright's staining, frozen sections were immersed in methanol for 10 minutes, Wright's stain for 2 minutes, and 4nmM $NaPO_4$, pH 6.5 for 5 minutes, followed by rising in water.

Reactivity with blood group A, B, H, Lewis$^a$, Lewis$^b$, X and Y determinants as described by Lloyd et al, PNAS 61: 1470 (1968), was determined by a solid phase enzyme-linked immunoassay as described by Lloyd et al, Immunogen 17: 537 (1983), except that the antigen preparations were dissolved in water.

BIOCHEMICAL ANALYSIS

Each antibody was tested for its ability to precipitate an antigen from the spent medium and from detergent-solubilized cell extracts after labeling by three methods: metabolic incorporation of [$^3$S]methionine Mattes, supra, or chloramine T $^{125}$I-labeling of solubilized cell membranes Mattes et al, Hybridoma 2: 253 (1983). In some experiments, cells were labeled with 0.5 mCi $H_2$ $^{35}SO_4$ in 10 ml Fischer's medium for mouse leukemia, 10% dialyzed FBS for 24 hours. NP40 solubilization of labeled cells followed Mattes, Hybridoma supra, and immunoprecipitation procedures as described by Mattes, PNAS, supra were followed. Briefly, 1.0 or 0.1 μl of mAb (serum from nude mice bearing the hydridoma) was mixed with labeled cell extracts. After 1 hour at 4°, 0.015 ml of rabbit antiserum to mouse IgG (heavy and light chains), was added and incubated overnight at 4°. *Staphylococcus aureus* (SA, 0.015 ml packed), was added in 1.0 ml. After 30 minutes at 4°, the SA was pelleted, washed four times and extracted with SDS sample buffer for analysis on acrylamide gels. To analyze low molecular weight proteins, modification of the method of Swank and Munkres, Anal Biochim 39: 162 (1977), was used preparing gels with 12.5% acrylamide, 1.25% bisacrylamide and 8 M urea. Molecular weight standards used were myoglobin (17,000), cytochrome c (12,384) and insulin (3,400 and 2,300). These gels were processed as for fluorography even though the antigen was $^{125}$I-labeled because 2,5-diphenyloxazole (PPO) incorporated in the gel reduced cracking while drying.

To test heat stability, labeled extracts were heated at 100° for 5 minutes; precipitated proteins were removed by centrifugation (7,000 rpm, 15 minutes), then standard immunoprecipitations were performed using the supernatant. Preparation of chloroform:methanol (C:M), 2:1 cell extracts and their use in inhibition assays has been described by Mattes et al, PNAS 81: 568 (1984). To determine whether the mucin-like molecule precipitated by Ab MQ49 was soluble in C:M, [$^3$H]glucosamine-labeled cells were pelleted and extracted with C:M, 2:1 for 1 hour at room temperature. After centrifugation for 10 minutes at 3,000 rpm, the pellet was extracted with the standard solubilization buffer, while the supernatant was dried by evaporation, then suspended in the same buffer. Both fractions were tested for antigens detectable by immuno-precipitation. Treatment of precipitated antigens with chondroitinase ABC followed Bumol et al, PNAS 79: 1245 (1982).

TARGET CELLS

The origin and culture of cell lines derived from human tumors, and of normal human fibroblasts and kidney epithelial cells have been described by Mattes et al, PNAS 81: 568 (1984). Monoclonal antibodies MU78 and MT334 were tested against a total of 148 cell lines, which included 21 melanomas, 17 astrocytomas, 5 neuroblastomas, 12 colon carcinomas, 11 lung carcinomas, 8 ovarian carcinomas, 2 uterine carcinomas, 4 pancreatic carcinomas, 2 prostate carcinomas, 9 bladder carconomas, 17 renal carcinomas, 5 breast carcinomas, 1 hepatoma, 1 bile duct carcinoma, 1 choriocarcinoma, 9 B cell lymphomas or leukemias, 8 T cell lymphomas or leukemias, 6 null cell leukemias, 3 myeloid leukemias, 2 normal adult fibroblast cultures, 1 normal fetal fibroblast culture, and 3 normal kidney epithilial cell cultures. Ab MQ49 was tested against a total of 113 cell lines, which included 11 melanomas, 11 astrocytomas, 4 neuroblastomas, 11 colon carcinomas, 8 lung carcinomas, 7 ovarian carcinomas, 2 uterine carcinomas, 3 pancreatic carcinomas, 3 bladder carcinomas, 10 renal carcinomas, 8 breast carcinomas, 1 hepatoma, 1 bile duct carcinoma, 1 choriocarcinoma, 1 teratocarcinoma, 13 B cell lymphomas and leukemias, 4 T cell lymphomas and leukemias, 4 null cell leukemias, 2 myeloid leukimias, 2 myelomas, 2 normal adult fibroblast cultures and 4 normal kidney epithelial cell cultures.

RESULTS

SELECTION OF HYBRIDOMAS

The antibodies described herein were produced from three fusions using spleen cells from mice immunized with SW626 or SK-OV-4 human ovarian carcinoma cell lines. The initial screening was performed on a panel of cell lines which included the immunizing line, 3 melanomas and 3 astrocytomas. Hybridomas that produced monoclonal antibodies which appeared to be specific for the immunizing cell line were subcloned, expanded and tested further for specificity. The antibodies described herein were selected on the basis of their limited expression on normal tissue sites, and their ability to immunoprecipitate the antigen recognized. None of the antigens could be detected on erythrocytes. The antibodies did not react with ovarian cyst glycoproteins carrying A, B, H, I, X, Y or Lewis determinants.

MU78

Two antibodies (Ab MT263 and Ab MU78), from 2 different fusions, appear to recognize the same antigen since their distribution and biochemical characteristics are identical. Both fusions utilized mice immunized with SK-OV-4. Ab MT263 is an IgG1 and Ab MU78 is an IgG2b. MU78 precipitated an antigen from $^{125}$I-labeled samples, but not from [$^{35}$S]methionine or [$^3$H]glucosamine-labeled samples, which migrated at the dye front on 12.5% acrylamide gels. On urea-modified acrylamide gels, which fractionate low molecular weight proteins (Swank, supra), the antigen had a relative mobility of about 0.57 as is shown by FIG. 1, suggesting that the antigen is a protein of approximately 2-5,000 daltons. It is noted that in urea-modified acrylamide gels the correlation between MW and relative mobility is not as close as in standard SDS-PAGE (Swank, supra). When immunoprecipitates were run without reduction, there was no change in the mobility of MU78 in urea-modified acrylamide gels, indicating a lack of interchain disulfide bonds.

In tissue culture cell lines MU78 was detected by immunoperoxidase staining in the cytoplasm of a wide variety of carcinomas, including ovarian, colon, lung, pancreas, prostate, bladder, breast and bile duct as is shown in Table I. Seventeen renal carcinoma cell lines were negative, as were 5 neuroblastomas, 17 astrocytomas, 26 leukemias and lymphomas, 20 of 21 melanomas, 3 lines of normal fibroblasts and 3 lines of normal kidney epithelial cells. The most common strongly positive cell types were carcinomas of the lung (3/11 positive) and colon (5/12 positive), while other carcinoma types were less frequently positive. Two of 5 ovarian carcinoma cell lines, including the immunizing cell line, were positive. This antigen was also detected on the cell surface by a rosetting assay.

Figure 2:
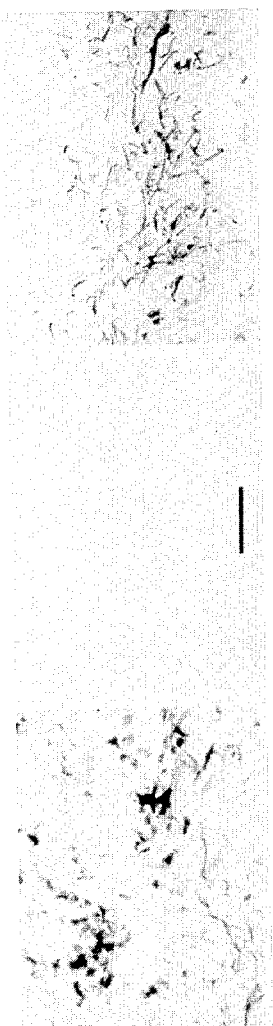
FIG. 2 shows photomicrographs of 5$\mu$m cryostat sections of normal human tissues, as follows: (A): skin-upper dermis; (B): skin-lower dermis; (C): primary bronchus, subepithelial; (D): colon; (E): sweat gland. In each series, the left hand photograph shows staining with Wright's stain or hematoxylin (E), to show morphology; center shows immunoperoxidase staining with negative monoclonal serum; right shows staining with immunoperoxidase plus MU78 (A,B,C), MT334 (D), or MQ49 (E). Magnifications: A, B, E×312; C×500; D×125.
Figure 2:
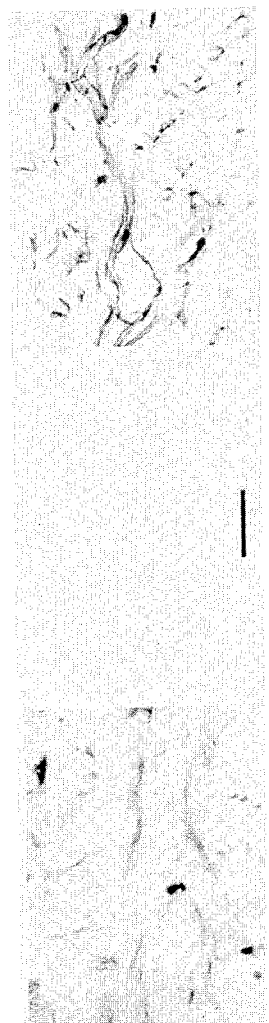
Figure 2:
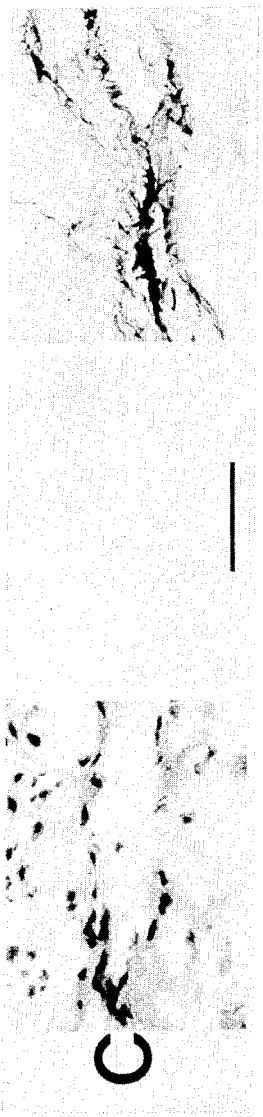
Figure 2:
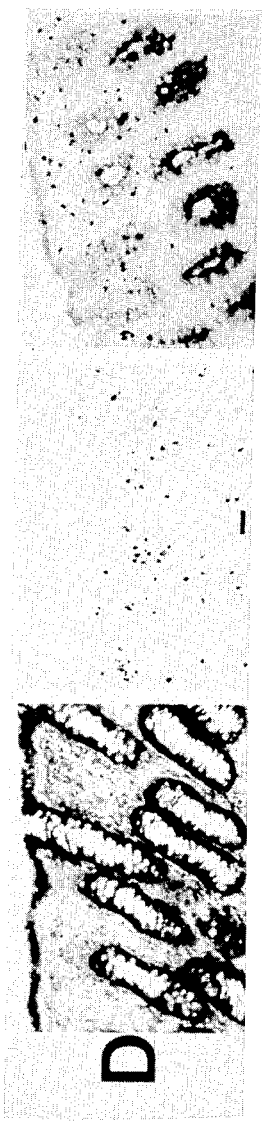
Figure 2:
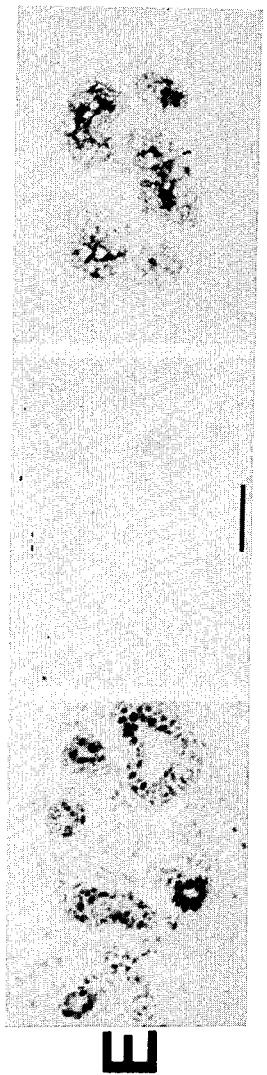

In frozen sections, monoclonal antibody MU78 stained fibers in the submucosa of the esophagus, stomach, colon, bronchus and ureter, in the connective tissue of the skin, breast and thyroid, and in the connective tissue separating smooth muscle fibers. The typical appearance of these fibers is demonstrated in FIG. 2A, which shows the upper region of the dermis. Deeper in the dermis, the fibers stained were considerably thicker (FIG. 2B). In the lamina propria of the bronchus and in the connective tissue separating smooth muscle fibers, the stained fibers seemed to form a braided or supercoiled structure (FIG. 2C). These fibers were clearly seen in tissue sections stained with Wright's stain (FIGS. 2A, 2B), appearing blue against the pink background of collagen fibers, while they were not resolved in sections stained with hematoxylin and eosin. Although the fibers stained with Ab MU78 resemble elastin fibers in their morphology and their distribution in soft connective tissue, elastin fibers in two different locations, the aorta and the elastic cartilage of the epiglotis, were negative. MU78 also stained two other locations not known to contain elastin fibers: in the ovary, in a very fine network of fibers throughout the stroma was stained; in the epidermis, the stratum granulosum only was lightly stained in a pattern which suggested very fine fibers but was not well resolved. It is noted that epithelial cells in tissue sections were negative, in contrast to the positive staining observed with many cultured carcinoma cell lines (Table I). In cultured cells the antigen shows a diffuse cytoplasmic, not fibrillar, distribution.

MT334

Ab MT334, an IgG1 antibody, precipitated an antigen labeled with [$^3$H]glucosamine but not with [$^{35}$S]methionine or $^{125}$I. This antigen was detected in spent medium from SK-OV-4 but not in solubilized cell extracts, and is therefore mainly a shed or secreted antigen. The antigen remained at the top of a 7.5% acrylamide gel, indicating a MW of more than 300,000 (FIG. 1). The antigen was still precipitated after treating a labeled antigen preparation at 100° C. for 5 minutes, which suggests that the determinant recognized is carbohydrate in nature. MT334 is not sulfated, suggesting that it is a mucin-like molecule rather than a proteoglycan.

In cell lines, MT334 was detected in the cytoplasm of a large fraction of carcinoma cell lines including those from ovary, colon, lung, pancreas, prostate, bladder, breast, liver and bile duct (Table II), using the immunoperoxidase method. All 17 renal carcinomas were negative, as were 5 neuroblastomas, 21 melanomas, 17 astrocytomas, 26 leukemias 3 cultures of normal fibroblasts and 3 cultures of normal kidney epithelial cells. MT334 was also detected on the cell surface using rosetting methods.

In frozen tissue sections, MT334 was detected in only one location—the base of the glands of the colon (FIG. 2D), which consists primarily of mucus-producing goblet cells. The antigen was concentrated on the luminal side of the cells, suggesting that it is a secretory product.

MQ49

MQ49 was originally detected as a cell surface antigen by rosetting assays. It was subsequently found that antibody MQ49 also reacted with cytoplasmic antigen. Ab MQ49 (an IgM antibody) precipitated an antigen from cells labeled with [$^3$H]glucosamine which is similar to MT334 in its biochemical properties: it remained at the top of a 7.5% acrylamide gel (FIG. 1) and was still precipitated after treatment at 100° C. for 5 minutes. However, unlike MT334, the antigen was also labeled by $^{35}SO_4$. Chondroitinase treatment of labeled immunoprecipitates had no effect on the molecular weight indicating that MQ49 is probably a sulfated mucin-like molecule. Reactivity with Ab MQ49 was not affected by neuraminidase treatment of the target cells. Also, unlike MT334, MQ49 was precipitated from solubilized cell extracts but not from spent medium. MQ49 was also detected in a lipid fraction prepared by chloroform:methanol extraction, using an assay detecting inhibition of rosetting. These data strongly suggest that Ab MQ49 recognizes a carbohydrate structure that is present on both a glycolipid and a mucin. To further support this interpretation, it was determined that the immunoprecipitated mucin-like antigen was not extracted by chloroform:methanol. MQ49 was also bound and specifically eluted from a wheat germ agglutinin affinity column.

On cell lines, MQ49 was detected on the surface of many carcinomas, including ovarian, renal, colon, breast, lung, uterine and pancreatic and a teratocarcinoma (Table 1). All 4 neuroblastomas, 11 melanomas, 11 astrocytomas and 25 leukemias or lymphomas were negative, as were 2 cultures of normal fibroblasts and 4 cultures of normal kidney epithelial cells. The most strongly positive carcinoma type was colon (7/11 positive).

In frozen tissue sections, MQ49 was detected in many types of secretory epithelial cells, including sweat glands of the skin, mucinous glands of the stomach and epithelial cells of the colon, pancreas, esophagus, ureter and breast (FIG. 2E). Hassal's corpuscles in the thymus were also stained. Staining was often localized at the luminal side of the cells, suggesting that the antigen is a secretory product.

MU78 stained fibrous structures resembling elastin fibers in connective tissue underlying epithelia or separating smooth muscle fibers. However, elastin fibers in tissues other than soft connective tissue, namely the aorta and elastic cartilage of the epiglottis, were negative. In sections of the epiglottis, fibers in the submucosa, similar to those in other tissues, were positive. Biochemical differences between these types of elastin fibers have not been described. The major component of elastin fibers is elastin, a 70,000 dalton protein which is responsible for the physical properties of the fibers. It is synthesized by fibroblasts, smooth muscle cells, and endothelial cells in vitro. Elastic is cross-linked within a scaffolding of microfibrils, which are composed of glycoproteins that are poorly defined, and which together constitute approximately 8% of the total proteins of elastin fibers. Antigen MU78, it is suggested, is an elastin-associated protein, possibly a component of microfibrils, which is present on a subset of elastin fibers, namely those in soft connective tissue. In addition, two locations were stained by monoclonal antibody MU78 which are not known to have elastin fibers. In the ovary, a dense network of very fine fibers, more dense than that in connective tissue, was positive, and in the stratum granulosum of the skin a narrow band of staining was observed. Microfibrils without associated elastin, but otherwise similar to the microfibrils in elastin fibers, have been described, and are considered by some investigators to have a unique functional role, rather than simply being precursors of elastin fibers. See, e.g., Cotta-Pereira et al, Adv. Exp. Med. Biol. 79: 19 (1977). Such fibers have not been described, however, in the locations stained by monoclonal antibody MU78. The ovarian stroma has dense reticular fibers, morphologically similar to the reticular fibers in the spleen, lymphnode and liver. Reticular fibers in the spleen and liver contain collagen type III as is shown by von der Mark, Int. Rev. Connect. Tissue Res. 9: 265 (1981). Based on the results with monoclonal antibody MU78, which does not stain the spleen, lymph node or liver we speculate that the fibers in the ovary are different from other reticular fibers in that they contain MU78. The staining of the stratum granulosum in the skin was not well resolved microscopically; the stained structures could be either cytoplasmic or extracellular, and could consist of densely packed, thin fibers. Further work is required to define the relationship of MU78 to elastin and reticular fibers. Recently, a non-elastin component of elastin fibers (clearly distinct from MU78) was reported, namely, serum amyloid P component (SAP), which was identified by immunofluoroescence with a specific antiserum. See Breathnach et al, Nature 293: 652 (1981).

In epithelial cancer cell lines, MU78 appears to be a protein of MW 2-5,000 daltons. Lipids are also labeled by iodination, but it is unlikely that a lipid would migrate like MU78 in urea-modified SDS-PAGE. MU78 was detected in the cytoplasm of many cultured carcinomas, but was not detected in any normal epithelial cells in cryostat sections with the possible exception of the stratum granulosum of the skin. Since cultured fibroblasts and other non-epithelial cells were negative for MU78, it seems likely that the source of the antigen in vivo is the epithelial cells adjacent to the connective tissue; their failure to be stained in sections may reflect a low intracellular concentration in vivo. In preliminary studies on sections of ovarian carcinomas it is noted that 8/10 specimens demonstrated cytoplasmic staining with Ab MU78. This suggests that the amount of antigen is markedly increased in tumor cells relative to normal cells of the same histological type. In these tumor sections cytoplasmic staining, but no stained fibers are observed.

MQ49 and MT334 both appear to be distinct carbohydrate determinants present on mucin-like macromolecules; MQ49 is also present on glycolipids. Antibody 19.9, described supra, identifies an antigen which was found to be a serum marker for pancreatic, colon and gastric carcinoma. MQ49 and 19.9 are similar in many respects and by sequential immunoprecipitation, it has been shown that both antigens are carried on the same molecules. This, however, does not necessarily mean that the determinants recognized are the same, as mucins are known to carry many different carbohydrate structures. Expression of MQ49 was found to correlate very well with expression of 19.9 in cultured cell lines; this, however, may reflect the ability of the cells to produce mucins, which carry many different antigenic determinants. Since MQ49 reactivity with cell lines was not affected by neuraminidase, it is concluded that MQ49 and 19.9 are different determinants. Ca.1 antigen, also described supra, is also very similar to MQ49 in its biochemical properties; however, its tissue distribution appears different, in that it was detected only in the epithelium of the bladder and fallopian tube.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

about 2–5 kilodaltons, and being distributed in carcinoma cytoplasm.

2. An isolated substantially pure antigen reactive with monoclonal antibody MT334 produced by a hybridoma deposited under ATCC No. HB 9751, said antigen being a glycoprotein molecule having a molecular weight of about 300 kilodaltons and being distributed on carcinoma cell surfaces.

3. An isolated substantially pure antigen reactive with monoclonal antibody MQ49 produced by a hybridoma deposited under ATCC No. HB 9750, said antigen being a sulfated glycoprotein molecule having a molecular weight of about 300 kilodaltons and being a secretory product of secretory epithelial cells and being distributed on carcinoma cell surfaces.

4. A method of determining the presence of carcinogenic tissue in a tissue sample, comprising contacting a tissue sample with at least one monoclonal antibody selected from the group consisting of MU78 (ATCC No. HB 9752, MT334 (ATCC No. HB 9751), and MQ49

TABLE 1

| Reactivity of moAbs with positive cell lines[a] | | | | | | | |
|---|---|---|---|---|---|---|---|
| | MU78 | MT334 | MQ49 | | MU78 | MT334 | MQ49 |
| Colon carcinomas | | | | Renal carcinomas | | | |
| SK-CO-1 | 4[b] | 3 | — | SK-RC-17 | 0 | 0 | + |
| SK-CO-10 | — | — | 5 | SK-RC-24 | 0 | 0 | + |
| SK-CO-13 | 0 | 1 | — | SK-RC-29 | 0 | 0 | + |
| SW403 | — | — | 4 | SK-RC-39 | — | — | 3 |
| SW480 | 0 | 3 | 4 | Bladder carcinomas | | | |
| SW620 | 0 | 3 | 5 | Scaber | 2 | 2 | 0 |
| SW1116 | 3 | 1 | 4 | RT4 | 0 | 3 | 0 |
| SW1222 | 0 | 3 | 4 | VM-CUB-2 | 2 | 1 | — |
| SW1417 | 2 | 3 | + | 5637 | 0 | 2 | — |
| HT-29 | 0 | 2 | 4 | JON | 3 | 1 | — |
| CaCO-2 | 3 | 0 | — | SW780 | 0 | 2 | 0 |
| 4J | 5 | 4 | — | Pancreas carcinomas | | | |
| Ovarian carcinomas | | | | CAPAN-1 | 0 | 2 | 0 |
| SK-OV-3 | 0 | 2 | 0 | CAPAN-2 | 0 | 2 | 5 |
| SK-OV-4 | 2 | 4 | + | A3 | 1 | 3 | — |
| SW626 | 0 | 3 | 4 | Prostate carcinomas | | | |
| A7 | 3 | 0 | — | DU145 | 2 | 0 | — |
| A10 | 0 | 1 | 0 | PC-3 | 4 | 2 | — |
| Uterine carcinomas | | | | Hepatoma | | | |
| SK-UT-1 | 0 | 1 | 4 | SK-HEP-1 | 0 | 1 | 0 |
| ME180 | 0 | 2 | — | Bile duct carcinoma | | | |
| | | | | Charles | 4 | 4 | 0 |
| Lung carcinomas | | | | Breast carcinomas | | | |
| SK-LC-2 | 0 | 1 | — | SK-BR-7 | 1 | 0 | — |
| SK-LC-3 | 3 | 4 | — | MCF-7 | 2 | 3 | 0 |
| SK-LC-4 | 1 | 0 | — | MDA-MB-231 | 0 | 4 | 0 |
| SK-LC-5 | 3 | 3 | — | BT20 | — | — | + |
| SK-LC-7 | 4 | 2 | — | CAMA | — | — | 3 |
| SK-LC-8 | 1 | 2 | — | Melanoma | | | |
| SK-LC-9 | 3 | 1 | — | SK-MEL-37 | 2 | 0 | 0 |
| SK-LC-11 | 4 | 4 | — | | | | |
| SK-LC-12 | 3 | 3 | — | | | | |
| SK-LC-LL | — | — | 4 | | | | |

TABLE 1 FOOTNOTES
[a]MU78 and MT334 were tested against 148 cell lines for intracellular reactivity on fixed target cells using the immunoperoxidase assay. MQ49 was tested against 113 cell lines for cell surface reactivity using a rosetting assay. Only cell lines that were positive with at least one of the moAbs are listed here; other target cell lines are described in Materials and Method.
[b]O indicates no reactivity at the highest concentration tested (1/500 for MU78 and MT334; 1/1,000 for MQ49). + indicates a positive reaction but with less than 50% rosetting at the highest concentration tested. — indicates not tested. The numbers show $\log_{10}$ (reciprocal titer) for MQ49, and $\log_5$ (reciprocal titer/125) for MU78 and MT334. The titer listed for peroxidase assays is the highest dilution producing definite reactivity. The titer for rosetting assays is the highest dilution producing at least 50% rosetting.

We claim:

1. An isolated substantially pure antigen reactive with monoclonal antibody MU78 produced by a hybridoma deposited under ATCC No. HB 9752, said antigen being a protein molecule having a molecular weight of (ATCC No. HB 9750), the monoclonal antibody being charcterized by non-reactivity with Lewis determinants, under conditions favoring formation of an antigenantibody complex and determining formation of said complex which indicates presence of carcinogenic tissue.

5. The method of claim 4, wherein said monoclonal antibody comprises MU78 (ATCC No. HB 9752) and the tissue sample is selected from the group consisting of lung, prostate, bladder, and bile duct tissue.

6. The method of claim 4, wherein said monoclonal antibody comprises MT334 (ATCC No. HB 9751) and the tissue sample is selected from the group consisting of lung, prostate, bladder, breast, liver, and bile duct tissue.

7. The method of claim 4, wherein said monclonal antibody comprises MQ49 (ATCC No. HB 9750) and the tissue sample is selected from the group consisting of uterine, lung, and teratocarcinoma tissue.

8. A hybridoma cell line which produces monoclonal antibody MU78 and is deposited with the ATCC under Accession Number HB 9752.

9. Monoclonal antibody MU78 produced by the hybridoma cell line of claim 15.

10. A hybridoma cell line which produces monoclonal antibody MT and is deposited with the ATCC under Accession Number HB 9751.

11. Monoclonal antibody MT334 produced by the hybridoma cell line of claim 10.

12. A hybridoma cell line which produces monoclonal antibody MQ 49 and is deposited with the ATCC under Accession Number HB 9750.

13. Monoclonal antibody MQ49 produced by the hybridoma cell line of claim 12.

* * * * *